United States Patent
Peuchert et al.

(10) Patent No.: US 11,078,108 B2
(45) Date of Patent: Aug. 3, 2021

(54) OPEN-PORE SINTERED GLASSES FOR USE IN ELECTRONIC CIGARETTES

(71) Applicant: SCHOTT AG, Mainz (DE)

(72) Inventors: Ulrich Peuchert, Bodenheim (DE); Norbert Greulich-Hickmann, Mainz (DE); Philipp Treis, Münster-Sarmsheim (DE); Yvonne Menke, Wiesbaden (DE); Michael Kluge, Offenbach an Main (DE)

(73) Assignee: SCHOTT AG, Mainz (DE)

(*) Notice: Subject to any disclaimer, the term of this patent is extended or adjusted under 35 U.S.C. 154(b) by 333 days.

(21) Appl. No.: 15/893,584

(22) Filed: Feb. 10, 2018

(65) Prior Publication Data
US 2018/0162769 A1 Jun. 14, 2018

Related U.S. Application Data

(63) Continuation of application No. PCT/EP2016/068400, filed on Aug. 2, 2016.

(30) Foreign Application Priority Data

Aug. 10, 2015 (DE) .......................... 102015113124.2

(51) Int. Cl.
*C03C 11/00* (2006.01)
*A61M 15/06* (2006.01)
(Continued)

(52) U.S. Cl.
CPC .............. *C03C 11/00* (2013.01); *A24F 40/42* (2020.01); *A61L 9/03* (2013.01); *A61M 11/042* (2014.02);
(Continued)

(58) Field of Classification Search
CPC ......... C03C 11/00; C03C 3/087; C03C 3/091; A61L 9/03; A61L 2209/13; A61M 11/042;
(Continued)

(56) References Cited

U.S. PATENT DOCUMENTS

| 4,588,540 A * | 5/1986 | Kiefer | ................ B01D 39/2075 264/43 |
| 5,573,984 A * | 11/1996 | Breitenbucher | ....... A01N 25/18 501/39 |

(Continued)

FOREIGN PATENT DOCUMENTS

| AT | 507187 | 3/2010 |
| CN | 101337769 | 1/2009 |

(Continued)

OTHER PUBLICATIONS

English translation of Written Opinion dated Nov. 3, 2016 for corresponding International Application No. PCT/EP2016/068400, 5 pages.

(Continued)

*Primary Examiner* — Noah S Wiese
(74) *Attorney, Agent, or Firm* — Ohlandt, Greeley, Ruggiero & Perle, L.L.P.

(57) ABSTRACT

A sintered body for use as a liquid reservoir in an electronic cigarette, medication administering devices, in thermally heated evaporators for fragrant substances is provided. The sintered body is made of open-pore sintered glass and has a porosity of greater than 50 vol %. The average pore size is in a range from 1 to 450 µm. The glass of the sintered body has a transition temperature $T_g$ of at least 450° C.

18 Claims, 4 Drawing Sheets

(51) Int. Cl.
*C03C 3/087* (2006.01)
*C03C 3/091* (2006.01)
*C03B 19/06* (2006.01)
*A61M 11/04* (2006.01)
*A24F 40/42* (2020.01)
*A61L 9/03* (2006.01)
*A24F 40/10* (2020.01)

(52) U.S. Cl.
CPC .............. *A61M 15/06* (2013.01); *C03B 19/06* (2013.01); *C03C 3/087* (2013.01); *C03C 3/091* (2013.01); *A24F 40/10* (2020.01); *A61L 2209/135* (2013.01)

(58) Field of Classification Search
CPC ....... A61M 15/06; A24F 47/008; A24F 47/00; C03B 19/06
See application file for complete search history.

(56) References Cited

U.S. PATENT DOCUMENTS

| | | | |
|---|---|---|---|
| 5,647,053 | A | 7/1997 | Schroeder |
| 2009/0011917 | A1 | 1/2009 | Goedeke |
| 2009/0126745 | A1* | 5/2009 | Hon ........................ H05B 3/03 131/273 |
| 2011/0226236 | A1 | 9/2011 | Buchberger |
| 2014/0060554 | A1 | 3/2014 | Collett |

FOREIGN PATENT DOCUMENTS

| | | |
|---|---|---|
| CN | 203841120 | 9/2014 |
| CN | 104768407 | 7/2015 |
| DE | 3305854 | 9/1984 |
| DE | 4417739 | 6/1995 |
| DE | 69631336 | 6/2004 |
| DE | 102006041042 | 3/2008 |
| EP | 2022350 | 2/2009 |
| EP | 2764783 | 8/2014 |

OTHER PUBLICATIONS

English translation of International Preliminary Report on Patentability dated Feb. 13, 2018 for corresponding International Application No. PCT/EP2016/068400, 6 pages.

English translation of International Search Report dated Nov. 3, 2016 for corresponding International Application No. PCT/EP2016/068400.

* cited by examiner

OPEN-PORE SINTERED GLASSES FOR USE IN ELECTRONIC CIGARETTES

CROSS REFERENCE TO RELATED APPLICATIONS

This application is a continuation of International Application No. PCT/EP2016/068400 filed on Aug. 2, 2016, which claims benefit under 35 U.S.C. § 119(a) of German Patent Application No. 10 2015 113 124.2 filed Aug. 10, 2015, the entire contents of both of which are incorporated herein by reference.

BACKGROUND

1. Field of the Invention

The invention generally relates to a liquid reservoir for hot applications. In particular, the invention relates to a liquid reservoir for storage and controlled release of evaporable substances for use in electronic cigarettes, in medication administering devices, and/or in thermally heated evaporators for fragrant substances, and also relates to an evaporator unit for evaporating liquids in electronic cigarettes, in medication administering devices, and/or in thermally heated evaporators for fragrant substances.

2. Description of Related Art

Electronic cigarettes, also referred to as e-cigarettes below, are increasingly being used as an alternative to tobacco cigarettes. Typically, electronic cigarettes comprise a mouthpiece and an evaporator unit. The evaporator unit has a liquid reservoir which is connected to a heating element.

Certain medications, in particular medications for treating the respiratory tract, and/or the oral and/or nasal mucosa are advantageously administered in evaporated form. Liquid reservoirs according to the invention can be used for storing and releasing such medications, in particular in administering devices for such medications. In this case, it is also possible that the liquid reservoir is connected to a heating element and thus forms at least part of an evaporator unit.

Thermally heatable evaporators are increasingly used to provide an ambience with fragrant substances, in particular in bars, hotel lobbies, and/or vehicle interiors, such as the interiors of motor vehicles, in particular automobiles. The evaporator unit used in this case also has a liquid reservoir connected to a heating element. The liquid reservoir contains a liquid which is usually a carrier liquid, such as propylene glycol or glycerol, in which additives are dissolved and/or, more generally, contained, such as fragrant and flavoring substances, and/or nicotine, and/or medications. The carrier liquid is bonded on the inner surface of the liquid reservoir by adsorption processes.

Generally, the liquid stored in the liquid reservoir is evaporated by the heating element, desorbed from the inner surface area of the liquid reservoir, and can be inhaled by the user. Here, temperatures of over 200° C. are temporarily reached.

Thus, the liquid reservoir has to exhibit high uptake capability and a high adsorption effect, but at the same time, however, the liquid has to be released rapidly at high temperatures.

From prior art, electronic cigarettes are known which have porous liquid reservoirs made of organic polymers. However, in case of excessive heating power, for example if the liquid reservoir runs dry in uncontrolled manner, temperatures might be reached during operation at which volatile substances are released from the liquid reservoir or decomposition of the liquid reservoir occurs. These substances might then be inhaled by the user.

Due to the low temperature stability of the polymeric material, it is therefore necessary to maintain a minimum spacing between the heating element and the liquid reservoir, which prevents a compact design of the evaporator unit and hence of the electronic cigarette.

As an alternative to maintaining a minimum spacing, a wick can be used that leads the liquid to be evaporated to the heating coil by capillary forces. This wick is usually made of glass fibers. Although these glass fibers exhibit high temperature stability, the individual glass fibers tend to break easily, however. The same applies if the liquid reservoir itself is made of glass fibers. Therefore, there is a risk that the user inhales loosened or partially dissolved fiber fragments.

SUMMARY

An object of the invention is to provide a liquid reservoir for use in electronic cigarettes and/or in medication administering devices and/or in thermally heated evaporators for fragrant substances, which does not have the drawbacks described above. A further object of the invention is to provide an improved evaporator unit for hot applications for evaporating carrier liquids, in particular for an electronic cigarette, medication administering devices, and/or thermally heated evaporators for fragrant substances.

The evaporator unit according to the invention for use in the aforementioned applications comprises a liquid reservoir and a heating element. A carrier liquid is stored in the liquid reservoir by adsorptive interactions, which carrier liquid may contain fragrant and flavoring substances and/or medications including active substances and/or nicotine dissolved in suitable liquids, for example. By means of the heating element, high temperatures are generated in the evaporator so that the carrier liquid is evaporated, desorbed from the inner surface area of the liquid reservoir, and the vapor can be inhaled by the user.

The liquid reservoir according to the invention comprises a sintered body made of open-pore sintered glass. The liquid is stored in the open pores of the sintered body. The term "open-pore sintered body" refers in particular to a sintered body in which at least 95% of the pore volume thereof are open pores.

The organic carrier liquid is adsorbed on the surface of the pores of the sintered body, i.e. on the inner surface area thereof. Preferably, in the loaded state prior to evaporation the weight of the carrier liquid in the liquid reservoir is at least 50% of the weight of the sintered body.

The carrier liquid is distinguished by good evaporability. Further substances can be dissolved in the organic carrier liquid, in particular flavoring substances, fragrant substances, medications, and/or nicotine. In one embodiment of the invention, the nicotine concentration in the carrier liquid is from 1 to 30 mg/ml, preferably from 2 to 20 mg/ml. The carrier liquid preferably contains propylene glycol, glycerol, and mixtures thereof as the main constituents.

The sintered body has a porosity of greater than 50 vol %, preferably of at least 60 vol %, more preferably of at least 70 vol %. Due to the high porosity, high adsorption capacity of the sintered body is ensured. Thus, according to one embodiment, the sintered body can adsorb propylene glycol in an amount of at least 50% of its weight at a temperature of 20° C. and in an adsorption time of 3 hours.

The average pore size of the sintered body is in a range from 1 to 450 μm. This average pore size has been found to be particularly advantageous in terms of the adsorption capacity and the desorption behavior at room temperature, as well as at high temperatures in the range of the evaporation point of the carrier liquid, in particular at temperatures of about 300° C.

If the pores of the sintered body are too small, the latter cannot take up sufficient carrier liquid. Although large pores are advantageous in terms of adsorption capacity, they simultaneously cause a high desorption rate at 20° C., i.e. under the storage conditions of a liquid reservoir for electronic cigarettes.

According to a refinement of the invention it is contemplated that the sintered body has a specific surface area of >0.5 m$^2$/g or even >0.8 m$^2$/g. The large specific surface area is thereby responsible for a high adsorption capacity. However, under certain circumstances, an excessive specific surface area may cause the carrier liquid to not be desorbed rapidly enough even at high temperatures, and/or may cause chromatography effects to occur. Chromatography effects are disadvantageous, because the various substances dissolved in the carrier liquid are desorbed at different times and thus the composition of the vapor will change during the operation of the aforementioned devices. Therefore, according to one embodiment of the invention, a specific surface area of smaller than 20 m$^2$/g or even smaller than 10 m$^2$/g is contemplated.

In addition to a high adsorption capacity, the sintered body in the form of a liquid reservoir has a low desorption rate at 20° C. Thus, according to one embodiment, not more than 15 wt % of the previously adsorbed liquid carrier medium, such as propylene glycol, is desorbed during a desorption time of 100 hours, which is particularly advantageous in terms of long-term stability. At the same time, at least 50% of the previously adsorbed mass of the liquid carrier medium, in particular propylene glycol, is desorbed at a temperature of 300° C. and a desorption time of 5 minutes here.

Thus, the liquid reservoir is suitable for use in hot applications, in particular in electronic cigarettes, and/or in medication administering devices, and/or in thermally heated evaporators for fragrant substances.

According to one embodiment of the invention, the average pore size is in a range from 5 to 400 µm. The average pore size may as well be in a range from 10 to 350 µm.

The sintered body may as well have a double pore structure. Here, a double pore structure refers to macropores with a pore size from 20 to 450 am which have open microscopic pores in their pore walls, which mostly have a size in a range from 1 to 10 µm.

The sintered body can be obtained by a method in which, first, fine-grained glass powder with grain sizes in a range of approximately 20 µm to 600 µm, preferably a maximum of 300 µm, is mixed with a high-melting coarse-grained salt and a binder. 5 to 20 wt % of fine-grained glass powder is added to this mixture, and the mass is pressed into shape. The resulting shaped body is heated to the sintering temperature of the glass and sintered. The melting temperature of the employed glass is above the respective sintering temperature, so that the grain structure of the salt is preserved. After the sintering process, the salt is washed out with a suitable solvent. The salts NaCl and K$_2$SO$_4$ have been found to be particularly suitable for this purpose. Other salts such as KCl, MgSO$_4$, Li$_2$SO$_4$, Na$_2$SO$_4$ are conceivable as well. Besides such aspects as costs, environmental compatibility or the like, the choice of the salt is determined by the glass that is employed and the temperature required for sintering same. According to one embodiment of the invention, 50 to 20 wt % of glass powder with a grain size from 15 to 60 µm and an aqueous polyethylene glycol solution are added to 50 to 80 wt % of salt with a grain size from 30 to 200 µm, and mixed thoroughly. The so obtained mixture can either be dried, or 5 to 20 wt % of glass powder (based on the mass of the mixture) can be added thereto in the moist state. The mixture is pressed into shape and sintered at the sintering temperature of the employed glass. Subsequently, the salt is washed out so that a porous sintered body is obtained.

As a result, a highly porous sintered body with open pores is obtained. Since the individual glass grains are firmly bonded to each other by the sintering process, the sintered body has a good mechanical strength compared to a corresponding glass fiber material, despite of its high porosity. Thus, the sintered body does not contain any loose or easily releasable particles which might be inhaled by the user when the sintered body is used as a liquid reservoir in an electronic cigarette and/or in a medication administering device and/or in thermally heated evaporators for fragrant substances. Due to the high mechanical stability of the sintered body, it is thus possible to provide liquid reservoirs which may even exhibit porosities of more than 80 vol %.

The sintered porous glass body is inert to carrier liquids as used in electronic cigarettes, and/or in medication administering devices, and/or in thermally heated evaporators for fragrant substances. Also, the employed glass has a transition temperature $T_g$ of at least 450° C. Due to the high transition temperature, the releasing behavior of the glass is very low, i.e. even at high temperatures glass constituents are not released or only to a very limited extent. In addition, it is possible to choose the composition of the glass so that it contains no or only very few volatile constituents.

In the case of an electronic cigarette, temperatures of significantly more than 200° C. are reached in the evaporator in the area of the heating coil, locally up to 500 to 600° C. Due to the low releasing property of the employed glass, a liquid reservoir made of the sintered body according to the invention can thus be positioned substantially closer to the heating element than would be possible with a liquid reservoir made of a polymeric material, for example. This is advantageous in terms of the design options of electronic cigarettes. For example, the electronic cigarette may have a more compact design, or the additional space available within the electronic cigarette may be used for other functions. According to one embodiment of the invention, the glass has a transition temperature $T_g$ of greater than 500° C. or even greater than 600° C. In one embodiment of the invention, the glass of the sintered body has transition temperatures of more than 700° C. The same applies to medication administering devices and/or to thermally heated evaporators for fragrant substances.

Glasses containing SiO$_2$ have been found to be particularly advantageous. Borosilicate glasses, aluminosilicate glasses, aluminoborosilicate glasses, or soda-lime glasses have proved to be particularly suitable.

According to one embodiment of the invention, the glass of the sintered body contains the following constituents (in wt % on an oxide basis):

| | |
|---|---|
| SiO$_2$ | 70 to 75 wt %; |
| Na$_2$O + K$_2$O | 12 to 16 wt %; |
| CaO | 8 to 11 wt %; |
| MgO | 0 to 5 wt %; and |
| Al$_2$O$_3$ | 0 to 2 wt %. |

According to a further embodiment of the invention, the glass contains the following constituents (in wt % on an oxide basis):

| | |
|---|---|
| SiO$_2$ | 70 to 85 wt %; |
| B$_2$O$_3$ | 5 to 15 wt %; |
| Alkali oxides | 3 to 7 wt %; |
| Alkaline earth oxides | 0 to 4 wt %; and |
| Al$_2$O$_3$ | 2 to 5 wt %. |

Glasses containing the following constituents have also proven to be advantageous:

| | |
|---|---|
| SiO$_2$ | 55 to 75 wt %; |
| Na$_2$O | 0 to 15 wt %; |
| K$_2$O | 2 to 14 wt %; |
| Al$_2$O$_3$ | 0 to 15 wt %; |
| MgO | 0 to 4 wt %; |
| CaO | 3 to 12 wt %; |
| BaO | 0 to 15 wt %; |
| ZnO | 0 to 5 wt %; and |
| TiO$_2$ | 0 to 2 wt %. |

According to a further embodiment of the invention, the glass contains the following constituents:

| | |
|---|---|
| SiO$_2$ | 30 to 85 wt %; |
| B$_2$O$_3$ | 0.5 to 20 wt %; |
| Al$_2$O$_3$ | 0 to 15 wt %; |
| Na$_2$O | 3 to 15 wt %; |
| K$_2$O | 2.5 to 15 wt %; |
| ZnO | 0 to 12 wt %; |
| MgO | 2 to 10 wt %; |
| BaO | 0 to 10 wt %; |
| TiO$_2$ | 0 to 10 wt %; and |
| CaO | 0 to 8 wt %, preferably max. 5 wt %. |

According to one embodiment, the glass is an aluminosilicate glass containing the following constituents:

| | |
|---|---|
| SiO$_2$ | 58 to 65 wt %; |
| B$_2$O$_3$ | 6 to 10.5 wt %; |
| Al$_2$O$_3$ | 14 to 25 wt %; |
| MgO | 0 to 5 wt %; |
| CaO | 0 to 9 wt %; |
| BaO | 0 to 8 wt %; |
| SrO | 0 to 8 wt %; |
| ZnO | 0 to 2 wt %; and with Σ(MgO + CaO + BaO) 8 to 18 wt %. |

According to another embodiment, the glass contains the following constituents:

| | |
|---|---|
| SiO$_2$ | 50 to 60 wt %; |
| B$_2$O$_3$ | 8 to 12 wt %; |
| Al$_2$O$_3$ | 8 to 12 wt %; and |
| BaO | 20 to 30 wt %. |

According to one embodiment, the glass contains the following constituents:

| | |
|---|---|
| SiO$_2$ | 75 to 85 wt %; |
| B$_2$O$_3$ | 8 to 18 wt %; |
| Al$_2$O$_3$ | 0.5 to 4.5 wt %; |
| Na$_2$O | 1.5 to 5.5 wt %; and |
| K$_2$O | 0 to 2 wt %. |

Furthermore, the glass exhibits high thermal resistance. According to one embodiment of the invention, it is contemplated that the glass has a coefficient of linear thermal expansion $\alpha_{20\text{-}300°\ C.}$ in a range from 2.5 ppm/K to 10.5 ppm/K, preferably in a range from 3.0 ppm/K to 10.0 ppm/K. As a result, the sintered body also exhibits high thermal shock resistance. In this respect, sintered bodies with thermal expansion coefficients of up to a maximum of 9.5 ppm/K have been found to be advantageous.

Due to the high transition temperatures of the glass used for the sintered body and its high temperature resistance, the heating element can be mounted close to the liquid reservoir in the evaporator, which allows for a compact design of the electronic cigarette and/or of medication administering devices and/or of thermally heated evaporators for fragrant substances.

Based on the fabrication process it is possible to adapt the form of the sintered body and hence also that of the liquid reservoir to any desired shape, which makes it possible to combine several functionalities in a single component. According to one embodiment of the invention, the functions of the liquid reservoir, a wick, an air suction passage, and the heating element can be implemented in a single component of the evaporator, which makes it possible to exactly adjust the heating power and thus to achieve improved temperature control.

In a further embodiment of the invention, the heating element is directly applied on the liquid reservoir. It can be applied on the surface of the liquid reservoir in the form of a metal foil or a metal wire, for example. According to another embodiment, the heating element is applied on the liquid reservoir as a metallic coating. The direct arrangement of the heating element on the sintered body is advantageous, since less energy is required if the heating element is applied directly on the liquid reservoir, which reduces battery consumption of the electronic cigarette. In addition, better temperature control can be achieved.

BRIEF DESCRIPTION OF THE DRAWINGS

The invention will now be explained in more detail by way of exemplary embodiments and FIGS. 1 to 9, wherein.

DETAILED DESCRIPTION

Table 1 shows six different exemplary embodiments of a sintered body according to the invention. The individual exemplary embodiments differ in terms of the composition of the sintered glass.

TABLE 1

COMPOSITION AND PROPERTIES OF EXAMPLES 1 TO 6

| Composition [wt %] | Example 1 | Example 2 | Example 3 | Example 4 | Example 5 | Example 6 |
|---|---|---|---|---|---|---|
| $SiO_2$ | 69 | 80 | 61 | 55 | 72.8 | 74.3 |
| $B_2O_3$ | 1 | 13 | 10 | 10 | | |
| $Al_2O_3$ | 4 | 2.5 | 18 | 10 | 0.2 | 1.3 |
| $Na_2O$ | 13 | 3.5 | | | 13.9 | 13.2 |
| $K_2O$ | 3 | 1 | | | 0.1 | 0.3 |
| BaO | 2 | | 3.3 | 25 | | |
| CaO | 5 | | 4.8 | | 9.0 | 10.7 |
| MgO | 3 | | 2.8 | | 4.0 | 0.2 |
| $\alpha_{(20-300)}$ [ppm/K] | 9.1 | 3.25 | 3.2 | 4.0 | 9.5 | 9.0 |
| Density [g/cm$^3$] | 2.5 | 2.2 | 2.43 | 2.80 | | |
| Tg [° C.] | 525 | 525 | 717 | 665 | 564 | 573 |

Figure 1A:
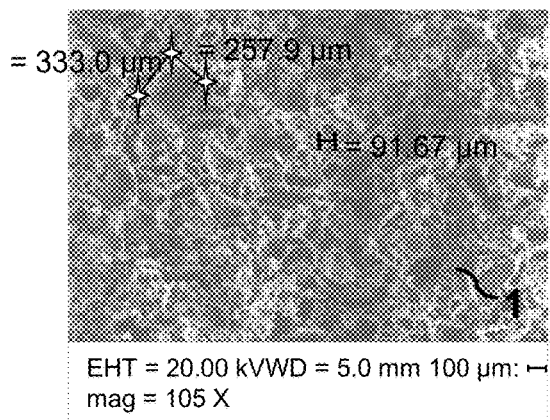
FIGS. 1a and 1b are SEM images of one embodiment of the sintered body according to the invention.
Figure 1B:
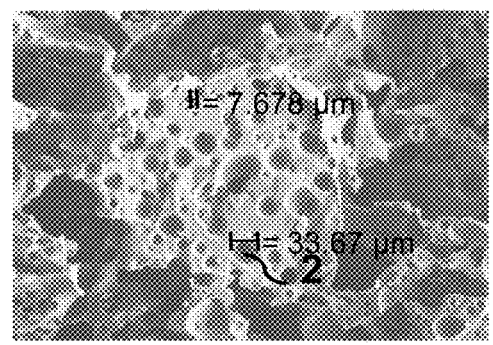

FIGS. 1a and 1b are SEM images (scanning electron micrographs) of an exemplary embodiment of the sintered body. The sintered body exhibits a very porous structure, both at the surface and at the breaking edge. Pores 1 are between 90 and 330 µm in size. In addition to the large open pores, the sintered body also has very small closed pores 2. For producing the exemplary embodiment of FIG. 1, NaCl was used as a salt.

Figure 2A:
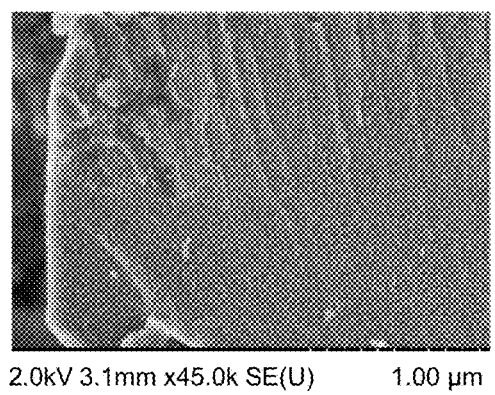
FIGS. 2a and 2b are SEM images of sintered glasses with different pore sizes as comparative examples.
Figure 2B:
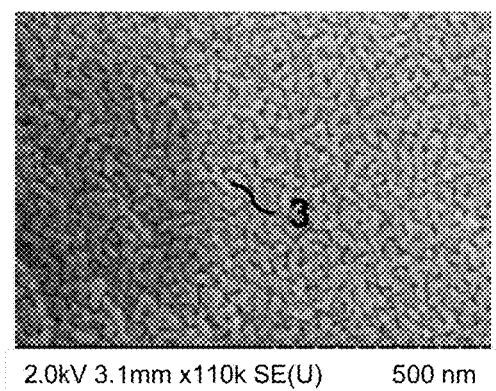
Figure 3A:
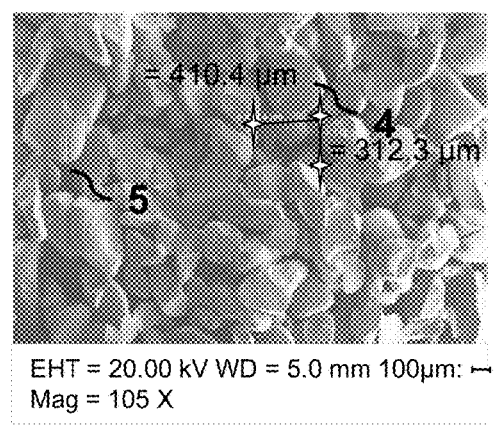
FIGS. 3a and 3b are SEM images of sintered glasses with different pore sizes as comparative examples.
Figure 3B:
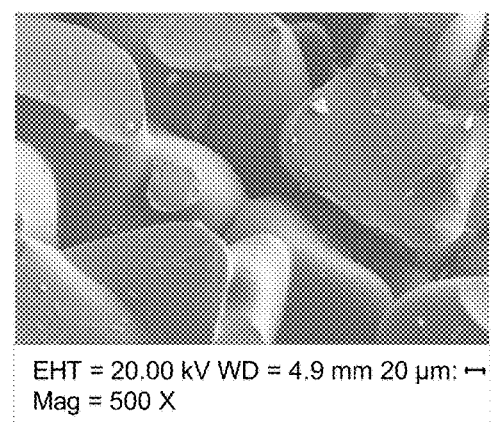

FIGS. 2a to 3b are SEM images of two different porous sintered glasses with different pore sizes. FIGS. 2a and 2b show SEM images of a porous sintered glass which has a multitude of very small pores. Pores 3 are only a few nanometers in size. The sintered glass of FIGS. 3a and 3b consists of many relatively large sintered glass grains 4. The intermediate spaces 5 between the individual glass grains 4 are very large here.

Figure 4:
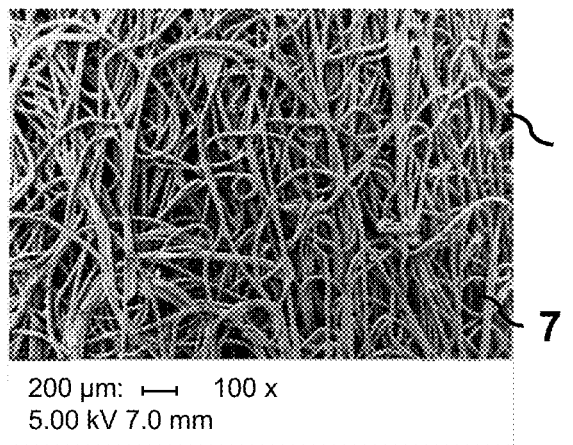
FIG. 4 is an SEM image of a liquid reservoir made of an organic polymeric material as a second comparative example.

FIG. 4 shows an SEM image of a liquid reservoir made of an organic polymer. The storage medium consists of entangled polymeric fibers 6. Thus, the liquid reservoir has a nonwoven structure. Between the individual fibers 6 there are many cavities 7 which can take up a carrier liquid.

Figure 5:
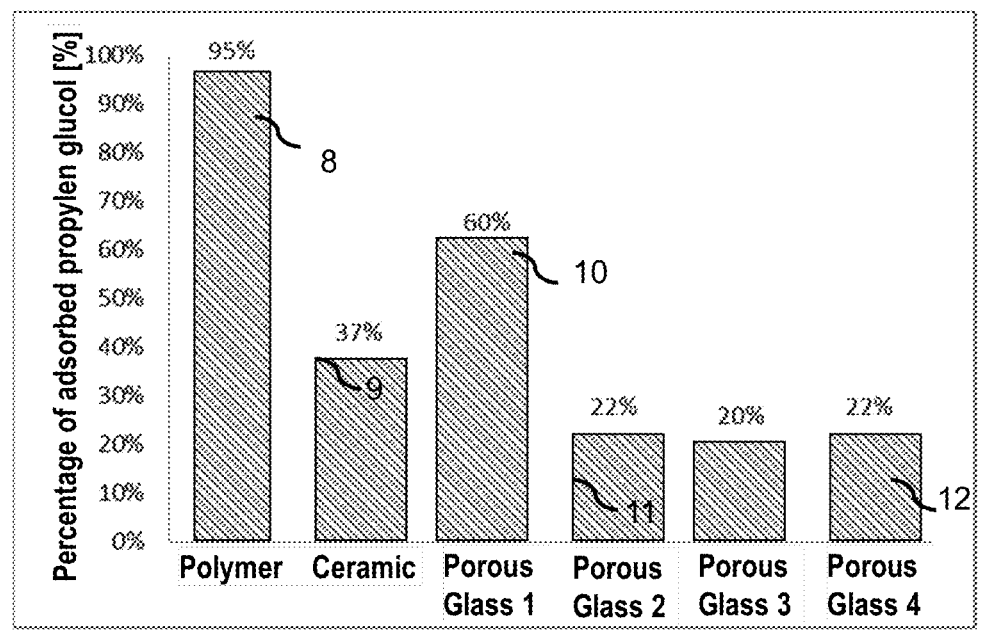
FIG. 5 is a graphical diagram showing the adsorption capacity of the exemplary embodiment and various comparative examples.

FIG. 5 illustrates the uptake capacity of liquid reservoirs. For this purpose, the different liquid reservoirs were soaked in propylene glycol for 3 hours, and then the mass increase was determined. Exemplary embodiment 10 corresponds to the sintered glass shown in FIG. 1. Comparative example 11 is the sintered glass of FIG. 3 with the pores of only a few nanometers in size. Comparative example 8 is the polymeric nonwoven of FIG. 4. Comparative example 9 is a sintered ceramic. Comparative example 12 has very large pores.

It will be apparent from FIG. 5, that a ceramic structure 9 can only take up a small amount of propylene glycol and is therefore not suitable as a liquid reservoir for use in electronic cigarettes and/or in medication administering devices and/or in thermally heated evaporators for fragrant substances.

In sintered glasses, uptake capacity depends on the pore size. Sintered glasses with very small pores 11 cannot take up enough propylene glycol, whereas in sintered glasses with excessively large pores 12 the specific surface area is too small to fully adsorb the uptaken propylene glycol. Therefore, a large proportion of the uptaken propylene glycol will flows out of the pores again. By contrast, the pores of exemplary embodiment 10 are large enough to take up enough propylene glycol and small enough to provide a sufficiently large specific surface area on which the propylene glycol can be adsorbed.

In addition to exemplary embodiment 10, the liquid reservoir of polymeric material 8 also exhibits high uptake capacity.

Figure 6:
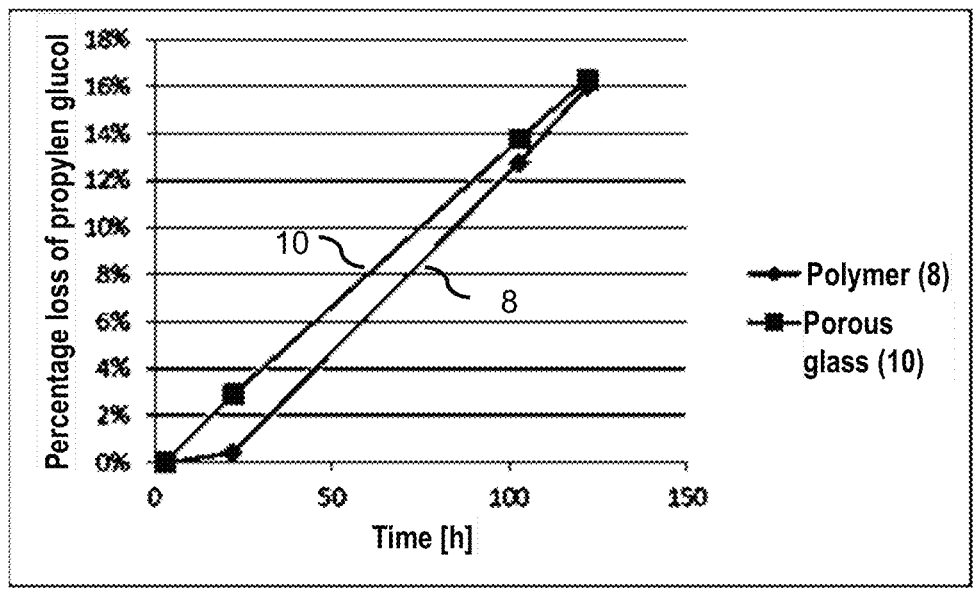
FIG. 6 is a graphical diagram of the desorption of one embodiment of a liquid reservoir according to the invention and a polymeric comparative example at 20° C.

FIG. 6 illustrates the results of a desorption test at 20° C. for the exemplary embodiment 10 and the polymeric liquid reservoir 8. For this purpose, the samples 8 and 10 soaked with propylene glycol were stored at a temperature of 20° C., and the mass loss of propylene glycol was measured as a function of time. Even after a period of 5 days, both the exemplary embodiment and the polymeric liquid reservoir show a loss of propylene glycol of less than 20 wt % of the previously uptaken propylene glycol.

Figure 7:
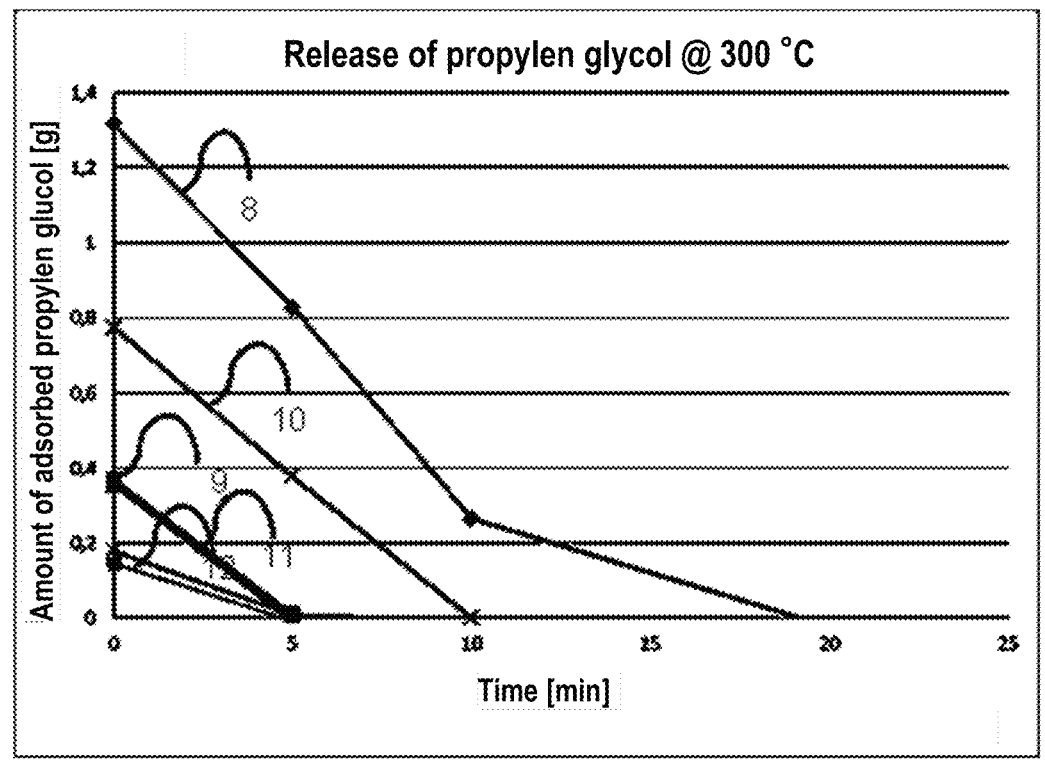
FIG. 7 is a graphical diagram of the desorption of one embodiment of a liquid reservoir according to the invention and the comparative examples at 300° C.

FIG. 7 illustrates desorption of propylene glycol at 300° C. For this purpose, the samples 8 to 12 were first soaked with propylene glycol and then dried at 300° C. in a furnace for 5, 10, 20, and 40 minutes. The mass loss of propylene glycol was determined with a balance. After 10 minutes, all samples had released the major proportion of propylene glycol. In exemplary embodiment 10, 50% of the propylene glycol had evaporated already after 5 minutes. While the polymeric sample 8 had melted as soon as after 5 minutes at 300° C., the exemplary embodiment withstands the high temperature load.

It will be obvious from FIGS. 5 to 7 that the liquid reservoir according to the invention is outstandingly suitable for use in an electronic cigarette and/or in medication administering devices and/or thermally heated evaporators for fragrant substances.

The underlying adsorption and desorption tests shown here are exemplary. Alternative determinations of the uptake and release capacity are manifold, e.g. quantitative tracking of coloring/discoloring of a body in contact with dyed propylene glycol.

Figure 8:
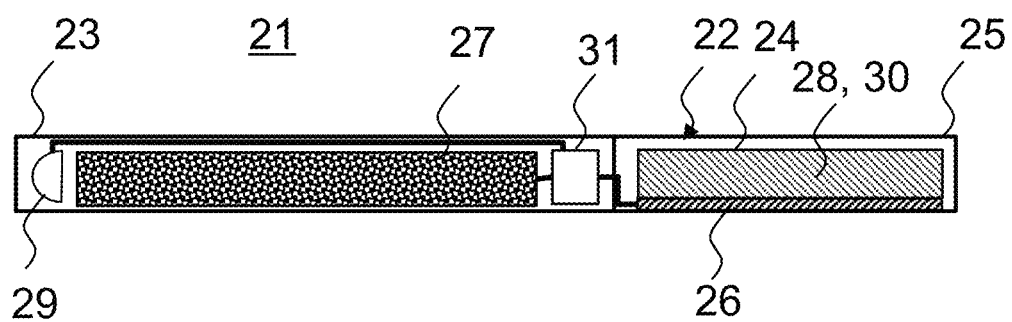
FIG. 8 is a schematic view of the configuration of an electronic cigarette.

FIG. 8 illustrates an electronic cigarette 21 according to the invention. Cigarette 21 comprises a tip 23 and a mouthpiece 25 on which the user drags to inhale the aerosol generated in the cigarette by means of an evaporator 22. According to a preferred embodiment of the invention, mouthpiece 25 is removable from tip 23.

Cigarette 21 comprises an electrical energy storage 27 in order to provide the electrical energy for evaporating the organic liquid in evaporator 22. In the illustrated embodiment, the electrical energy storage 27 is accommodated in the tip 23 of cigarette 21. Medication administering devices may have a similar configuration.

Electronic cigarette 21 further comprises a control unit 31 which controls the heating power for evaporator 22. In particular, the control unit 31 may be configured to check whether a user is inhaling and, depending thereon, to regulate the heating power of evaporator 22. Furthermore, a light-emitting diode 29 may be disposed in the tip 23, which is also controlled by control unit 31. When the control unit 31 detects that the user is dragging on cigarette 21, it can control the light-emitting diode 29 so that the light-emitting diode 29 lights up. Thus, a visual effect is achieved corresponding to the glowing when dragging on a conventional cigarette.

The evaporator unit 22 according to the invention includes a liquid reservoir 24 comprising a sintered body 28 and organic carrier liquid 10 adsorbed in the sintered body 28. The sintered body 28 has a specific surface area preferably in a range from 0.5 square meters per gram to a maximum of 10 square meters per gram. A specific surface area in this range leads to a high uptake capacity for carrier liquid 30 and at the same time still sufficient mechanical and thermal stability.

For heating the liquid reservoir 24 and thus for evaporating the organic carrier liquid 30 with constituents dissolved therein, such as nicotine, fragrant substances, and/or flavoring substances, the evaporator unit 22 comprises an electrically heatable heating element 26. Heating element 26 is supplied with power by electrical energy storage 27, controlled by control unit 31. By heating to an operating temperature of greater than 100° C., the organic carrier liquid 30 adsorbed in the sintered body 28, in particular a high-boiling alcohol such as glycerol or propylene glycol, can be evaporated. The sintered body 28 has a porosity of more than 50 vol % in order to be able to take up a large amount of carrier liquid and to be able to release the carrier liquid with the dissolved flavoring substances and/or stimulants, such as in particular nicotine, over a sufficiently long time.

The glass used for the sintered body 28 preferably has a coefficient of linear thermal expansion α in a range from 2.5 ppm/K (i.e. $2.5 \cdot 10^{-6} K^{-1}$) to 10.5 ppm/K, preferably in a range from 3.0 ppm/K to 10.0 ppm/K. Transition temperatures $T_g$ of greater than 450° C., in particular greater than 500° C. are particularly preferred. Suitable glasses are disclosed herein.

Figure 9:
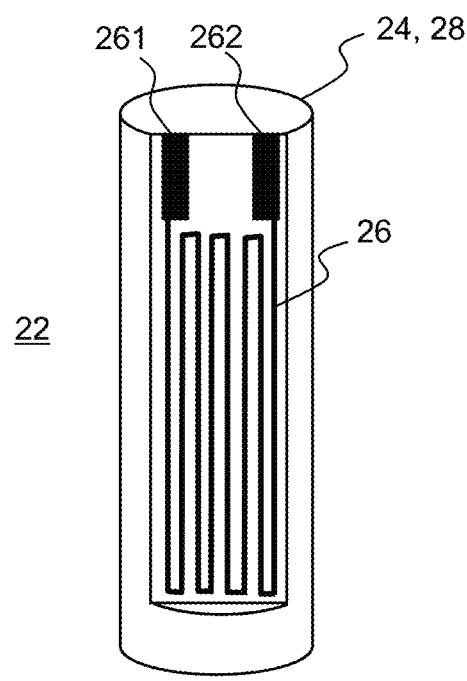
FIG. 9 is a schematic view of the configuration of one embodiment of the evaporator unit in which the heating element is directly arranged on the liquid reservoir.

FIG. 9 shows an exemplary embodiment of an evaporator unit 22 in which the heating element 26 is disposed directly on the sintered body 28. In particular, the heating element 26 is firmly connected to the sintered body 28. Such a connection can in particular be achieved if the heating element 26 is provided in the form of a sheet resistor. For this purpose, an electrically conductive sheet resistor type coating patterned in the form of a conductive path is applied onto the sintered body 28. A coating that is directly applied to the sintered body 28 as a heating element 26 is advantageous in order to achieve good thermal contact which provides for fast heating, inter alia. In the present illustrated example, enlarged contacts 261, 262 are provided in the conductive coating, at which the sheet resistor can be electrically contacted. The electrical connection can be established to mating contacts in the mouthpiece 25 when the liquid reservoir 24 is inserted, for example.

What is claimed is:

1. A sintered body for use as a liquid reservoir, comprising an open-pore sintered glass having a porosity of >50 vol % and an average pore size in a range from 90 to 450 µm, wherein the open-pore sintered glass comprises glass having a transition temperature of at least 450° C., wherein the open-pore sintered glass has a specific surface area that is at least 0.8 m²/g and smaller than 20 m²/g.

2. The sintered body as claimed in claim 1, wherein the open-pore sintered glass is configured for a use selected from the group consisting of an electronic cigarette, a medication administering device, and a thermally heated evaporator for a fragrant substance.

3. The sintered body as claimed in claim 1, wherein the open-pore sintered glass has a mass and adsorbs propylene glycol in an amount of at least 50% of the mass at a temperature of 20° C. and in an adsorption time of 3 hours.

4. The sintered body as claimed in claim 3, wherein the open-pore sintered glass is configured so that not more than 15 wt % of previously adsorbed propylene glycol is desorbed during a desorption time of 100 hours, and wherein the open-pore sintered glass desorbs at least 50% of the previously adsorbed propylene glycol at a temperature of 300° C. and a desorption time of 5 minutes.

5. The sintered body as claimed in claim 1, wherein the transition temperature is greater than 600° C.

6. The sintered body as claimed in claim 1, wherein the glass has a coefficient of linear thermal expansion a in a range from 2.5 ppm/K to 10.5 ppm/K.

7. The sintered body as claimed in claim 1, wherein the average pore size is in a range from 90 µm to 350 µm.

8. The sintered body as claimed in claim 1, wherein the porosity is at greater than 80 vol %.

9. The sintered body as claimed in claim 1, wherein the glass is selected from the group consisting of a borosilicate glass, an aluminosilicate glass, an aluminoborosilicate glass, and a soda-lime glass.

10. The sintered body as claimed in claim 1, wherein the glass comprises (in wt % on an oxide basis):

| | |
|---|---|
| $SiO_2$ | 70 to 75 wt %; |
| $Na_2O + K_2O$ | 12 to 16 wt %; |
| CaO | 8 to 11 wt %; |
| MgO | 0 to 5 wt %; and |
| $Al_2O_3$ | 0 to 2 wt %. |

11. The sintered body as claimed claim 1, wherein the glass comprises (in wt % on an oxide basis):

| | |
|---|---|
| $SiO_2$ | 70 to 85 wt %; |
| $B_2O_3$ | 5 to 15 wt %; |
| Alkali oxides | 3 to 7 wt %; |
| Alkaline earth oxides | 0 to 4 wt %; and |
| $Al_2O_3$ | 2 to 5 wt %. |

12. The sintered body as claimed in claim 1, wherein the glass comprises (in wt % on an oxide basis):

| | |
|---|---|
| $SiO_2$ | 50 to 75 wt %; |
| $Na_2O$ | 0 to 15 wt %; |
| $K_2O$ | 2 to 14 wt %; |
| $Al_2O_3$ | 0 to 15 wt %; |
| MgO | 0 to 4 wt %; |
| CaO | 3 to 12 wt %; |
| BaO | 0 to 15 wt %; |
| ZnO | 0 to 5 wt %; and |
| $TiO_2$ | 0 to 2 wt %. |

13. The sintered body as claimed in claim 1, wherein the glass comprises (in wt % on an oxide basis):

| | |
|---|---|
| $SiO_2$ | 30 to 85 wt %; |
| $B_2O_3$ | 0.5 to 20 wt %; |
| $Al_2O_3$ | 0 to 15 wt %; |
| $Na_2O$ | 3 to 15 wt %; |
| $K_2O$ | 2.5 to 15 wt %; |
| ZnO | 0 to 12 wt %; |
| MgO | 2 to 10 wt %; |
| BaO | 0 to 10 wt %; |
| $TiO_2$ | 0 to 10 wt %; and |
| CaO | 0 to 8 wt %. |

14. The sintered body as claimed in claim 1, wherein the specific surface area is smaller than 10 m²/g.

15. The sintered body as claimed in claim 1, wherein the open-pore sintered glass is configured for a use selected from the group consisting of an electronic cigarette and a thermally heated evaporator for a fragrant substance.

16. A sintered body for use as a liquid reservoir, comprising an open-pore sintered glass having a porosity of >50 vol % and an average pore size in a range from 1 to 450 μm, wherein the open-pore sintered glass comprises glass having a transition temperature of at least 450° C., wherein the glass comprises (in wt % on an oxide basis):

| | |
|---|---|
| $SiO_2$ | 50 to 60 wt %; |
| $B_2O_3$ | 8 to 12 wt %; |
| $Al_2O_3$ | 8 to 12 wt %; and |
| BaO | 20 to 30 wt %. |

17. The sintered body as claimed in claim 1, wherein the glass comprises (in wt % on an oxide basis):

| | |
|---|---|
| $SiO_2$ | 75 to 85 wt %; |
| $B_2O_3$ | 8 to 18 wt %; |
| $Al_2O_3$ | 0.5 to 4.5 wt %; |
| $Na_2O$ | 1.5 to 5.5 wt %; and |
| $K_2O$ | 0 to 2 wt %. |

18. A sintered body for use as a liquid reservoir, comprising an open-pore sintered glass having a porosity of >50 vol % and an average pore size in a range from 1 to 450 μm, wherein the open-pore sintered glass comprises glass having a transition temperature of at least 450° C., wherein the glass comprises (in wt % on an oxide basis):

| | |
|---|---|
| $SiO_2$ | 58 to 65 wt %; |
| $B_2O_3$ | 6 to 10.5 wt %; |
| $Al_2O_3$ | 14 to 25 wt %; |
| MgO | 0 to 5 wt %; |
| CaO | 0 to 9 wt %; |
| BaO | 0 to 8 wt %; |
| SrO | 0 to 8 wt %; |
| ZnO | 0 to 2 wt %; and a total of MgO, CaO, and BaO is 8 to 18 wt %. |

\* \* \* \* \*